(12) United States Patent
Inoue et al.

(10) Patent No.: US 10,966,879 B2
(45) Date of Patent: Apr. 6, 2021

(54) DISPOSABLE DIAPER

(71) Applicant: Unicharm Corporation, Shikokuchuo (JP)

(72) Inventors: Takuya Inoue, Kanonji (JP); Shunsuke Takino, Kanonji (JP); Hideaki Maki, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 444 days.

(21) Appl. No.: 15/740,840

(22) PCT Filed: May 13, 2016

(86) PCT No.: PCT/JP2016/064288
§ 371 (c)(1),
(2) Date: Dec. 29, 2017

(87) PCT Pub. No.: WO2017/002461
PCT Pub. Date: Jan. 5, 2017

(65) Prior Publication Data
US 2018/0214319 A1 Aug. 2, 2018

(30) Foreign Application Priority Data
Jun. 30, 2015 (JP) .............................. JP2015-132228

(51) Int. Cl.
*A61F 13/15* (2006.01)
*A61F 13/494* (2006.01)
(Continued)

(52) U.S. Cl.
CPC .... *A61F 13/4942* (2013.01); *A61F 13/15585* (2013.01); *A61F 13/49* (2013.01);
(Continued)

(58) Field of Classification Search
CPC ............ A61F 13/4942; A61F 13/15585; A61F 13/49; A61F 13/49017; A61F 13/494;
(Continued)

(56) References Cited

U.S. PATENT DOCUMENTS 4,695,278 A * 9/1987 Lawson ............ A61F 13/49426
604/385.27
6,120,488 A * 9/2000 VanRijswijck ....... A61F 13/494
604/364

(Continued)

FOREIGN PATENT DOCUMENTS

JP 11-290377 A 10/1999
JP 2002-522117 A 7/2002
(Continued)

OTHER PUBLICATIONS

International Search Report in PCT/JP2016/064288, dated Aug. 2, 2016, 4pp.

*Primary Examiner* — Jacqueline F Stephens
(74) *Attorney, Agent, or Firm* — Hauptman Ham, LLP

(57) ABSTRACT

A disposable diaper has front and rear waist regions, a crotch region, and an absorbent chassis. The absorbent chassis includes an absorbent structure and a pair of side flaps. Each of the side flaps has layered sheet materials and includes a distal edge, a cuff branch line between the side edge of the absorbent structure and the distal edge, a leg-opening elasticized area between the cuff branch line and the distal edge, and a leakage-barrier cuff branched from the cuff branch line and intersecting with the leg-opening elasticized area. The leakage-barrier cuff has a free edge parallelly-spaced from the cuff branch line. The distance from the cuff branch line to the distal edge is larger than from the cuff branch line to the free edge. The number of sheet material layers included in the leg-opening elasticized area is larger than in the leakage-barrier cuff.

1 Claim, 5 Drawing Sheets

(51) Int. Cl.
*A61F 13/49* (2006.01)
*A61F 13/496* (2006.01)

(52) U.S. Cl.
CPC .......... *A61F 13/494* (2013.01); *A61F 13/496* (2013.01); *A61F 13/49017* (2013.01); *A61F 2013/15878* (2013.01); *A61F 2013/4944* (2013.01)

(58) Field of Classification Search
CPC .......... A61F 13/496; A61F 2013/15878; A61F 2013/4944
USPC ............ 604/385.28, 385.24, 385.25, 385.26, 604/385.29, 385.3
See application file for complete search history.

(56) References Cited

U.S. PATENT DOCUMENTS

| | | |
|---|---|---|
| 6,248,097 B1 | 6/2001 | Beitz et al. |
| 2004/0215161 A1 | 10/2004 | Okuda et al. |
| 2008/0312631 A1 | 12/2008 | Okuda |
| 2014/0324010 A1 | 10/2014 | Oku et al. |

FOREIGN PATENT DOCUMENTS

| | | |
|---|---|---|
| JP | 2004-105697 A | 4/2004 |
| JP | 2007-20658 A | 2/2007 |
| JP | 2007-61462 A | 3/2007 |
| JP | 2013-48787 A | 3/2013 |
| JP | 2014-171688 A | 9/2014 |

\* cited by examiner

DISPOSABLE DIAPER

RELATED APPLICATIONS

The present application is a National Phase of International Application Number PCT/JP2016/064288, filed May 13, 2016, which claims priority to Japanese Application Number 2015-132228, filed Jun. 30, 2015.

TECHNICAL FIELD

The present disclosure relates to disposable diapers.

BACKGROUND ART

Conventionally, disposable diapers are well known. For example, Patent Literature 1 discloses a disposable diaper having a topsheet, a backsheet, an absorbent body and a pair of side sheets wherein the backsheet has a pair of outward extending parts extending in a lateral direction X beyond both end edges in the lateral direction of the topsheet. Of the paired side sheets, the parts laterally located to respective first joint parts, at which the respective side sheets are joined to the topsheet, are joined to the paired outward extending parts of the backsheet at second joint parts along the longitudinal direction of the outward extending parts. In addition, in the areas in which the paired side sheets are joined to the outward extending parts of the backsheet through the second joint parts, the paired side sheets respectively overlap in two or more layers on the side of the body-facing surface.

CITATION LIST

Patent Literature

PTL 1: Japanese Unexamined Patent Application Publication No. 2014-171688 (JP2014-171688)

According to the invention disclosed in PTL 1, the disposable diaper being capable of effectively preventing body exudates from leaking out is provided.

SUMMARY OF INVENTION

Technical Problem

However, in the disposable diaper disclosed in PTL 1, the free parts of the respective side flaps adapted to fit the inguinal region of the wearer, thereby functioning as the leakage-barrier cuffs have a length dimension larger than that of the fixed parts of the respective side flaps adapted to fit the wearer's thighs, thereby functioning as leg-gathers. Thus, during use of the disposable diaper, the movement of the wearer's legs may drag the free parts of the side flaps out from the diaper, thereby making it difficult for the free parts to function as the leakage-barrier cuffs. In addition, the number of thread-like elastic members arranged in the respective fixed parts to function as the leg-gathers is not enough to avoid a possibility that, during use of the diaper, the fixed parts may be accordion-folded in the lateral direction and may not properly fit around the wearer's thighs.

In view of the problem set forth above, an object of the present invention is to provide a disposable diaper having improved fittability.

Solution to Problem

The present invention is directed to a disposable diaper having a front waist region, a rear waist region and a crotch region located between the front and rear waist regions and includes a vertically long absorbent chassis extending to the front and rear waist regions centering on the crotch region.

In the disposable diaper according to the present invention, the absorbent chassis includes an absorbent structure and a pair of side flaps extending outward in the lateral direction from both side edges of the absorbent structure, each of the side flaps is formed of layered sheet materials and include a distal edge being spaced apart in the lateral direction from the side edge of the absorbent structure and extending in the vertical direction, a cuff branch line defined between the side edge of the absorbent structure and the respective distal edge so as to extend in the vertical direction, leg-opening elasticized area extending between the cuff branch line and the distal edge and leakage-barrier cuff branched from the cuff branch line and extending in a direction intersecting with the leg-opening elasticized area, the leakage-barrier cuff has a free edge parallelly-spaced in the lateral direction from the cuff branch line so as to extend in the vertical direction, a distance from the cuff branch line to the distal edge is larger than a distance from the cuff branch line to the free edge, and the number of sheet material layers included in the leg-opening elasticized area is larger than the number of the sheet material layers included in the leakage-barrier cuff.

According to one embodiment of the present invention, the leg-opening elasticized area includes three or more sheet material layers and these three or more sheet material layers are joined together by adhesive bonding or heat sealing. According to this embodiment, three or more sheet material layers included in the leg-opening elasticized area sufficiently enhance the stiffness of the leg-opening elasticized area to inhibit a possibility that the leg-opening elasticized area may be folded into a bellowslike shape in the lateral direction and thereby it is ensured that the leg-opening elasticized areas closely fit around a wide extent of the wearer's thighs.

According to one embodiment of the present invention, the leg-opening elasticized area includes at least three layers of the sheet material and at least four leg-elastic members joined by adhesive bonding or heat sealing under tension in the vertical direction between two layers of the sheet material being adjacent to each other among three layers and intervals in the lateral direction of the leg-elastic members are 6 mm or less. According to this embodiment, at least four leg-elastic members are arranged in each of the leg-openings elasticized areas at intervals of 6 mm or less to inhibit the possibility that the leg-opening elasticized area may be accordion-folded in the lateral direction, and thereby it is ensured that the leg-opening elasticized areas closely fit around a wide extent of the wearer's thighs.

According to one embodiment of the present invention, the leakage-barrier cuff is formed separately from the leg-opening elasticized area, each of the leakage-barrier cuffs includes two layers of the sheet material and at least one cuff-elastic member joined under tension in the vertical direction between two layers of the sheet material and at least one of the two layers of the sheet material extends into the leg-opening elasticized area so as to be included therein. According to this embodiment, at least one of two sheet material layers is included by the leg-opening elasticized area and functions to enhance the stiffness thereof sufficiently to inhibit a possibility that the elasticized area may constrict in the lateral direction as folded into a bellowslike shape. Thus, it is ensured that the leg-opening elasticized areas to closely fit around a wide extent of the wearer's thighs.

According to one embodiment of the present invention, at least one layer of the sheet material extending from the leakage-barrier cuff to the leg-opening elasticized area is adhesive bonded or heat sealed to the sheet material included in the leg-opening elasticized area. According to this embodiment, at least one sheet material layer extending from the leakage-barrier cuff to the leg-opening elasticized area is adhesive bonded or heat sealed to the leg-opening elasticized area, and whereby the stiffness of the leg-opening elasticized area is further enhanced to ensure that the leg-opening elasticized areas closely fit around a wide extent of the wearer's thighs.

According to one embodiment of the present invention, a region in which at least one sheet material extending in the lateral direction of the absorbent chassis to the leg-opening elasticized area overlaps with the leg-opening elasticized area has a width dimension at least 80% of the distance from the cuff branch line to the distal edge. According to this embodiment, the sheet material extending from the leakage-barrier cuff to the leg-opening elasticized area overlaps with at least 80% of the leg-opening elasticized area, and whereby further enhances the stiffness of the leg-opening elasticized area to inhibit the possibility that the leg-opening elasticized area may constrict in the lateral direction as folded into a bellowslike shape. Thus, it is ensured that the leg-opening elasticized areas closely fit around a wide extent of the wearer's thighs.

According to one embodiment of the present invention, the leakage-barrier cuff and the leg-opening elasticized area are bonded to each other with hot melt adhesives. In this way, the leakage-barrier cuff fit to the wearer's inguinal region, thereby further ensuring that the leg-opening elasticized areas closely fit around a wide extent of the wearer's thighs.

According to one embodiment of the present invention, a front end and a rear end of the absorbent chassis defined by both ends thereof in the vertical direction are respectively fixed to the front waist region and the rear waist region while parts of the leg-opening elasticized area located in the front end and the rear end are fixed to the front waist region and the rear waist region so as to be outward-directed in the lateral direction of the absorbent chassis, and parts of the leakage-barrier cuff located in the front end and the rear end are fixed to the front waist region and the rear waist region so as to be inward-directed in the lateral direction of the absorbent chassis. By fixing the leg-opening elasticized area so as to be outward-directed and fixing the leakage-barrier cuff so as to be inward-directed. This makes it possible to prevent the leakage-barrier cuff from projecting outward beyond the leg-opening elasticized area.

Advantageous Effects of Invention

According to one or more embodiments of the present invention, a distance from the cuff branch line to the distal edge is larger than a distance from the cuff branch line to the free edge and, in consequence, a possibility that the movements of the wearer's legs may drag the leakage-barrier cuffs out from the diaper. In addition, the number of sheet material layers included in the leg-opening elasticized area is larger than the number of sheet material layers included in the leakage-barrier cuff and, in consequence, a possibility that the leg-opening elasticized area may constrict in the lateral direction as folded into a bellowslike shape. In this way, the disposable diaper having its fittability improved is provided.

BRIEF DESCRIPTION OF DRAWINGS

The drawings illustrate specific embodiments of the present invention, including optional and preferred embodiments as well as essential features of the invention.

DESCRIPTION OF EMBODIMENTS

The embodiments described below relate to a disposable diaper 10 (hereinafter referred to as diaper (10)) including both optional and preferred features as well as these features which are essential features of the present invention.

Figure 1:
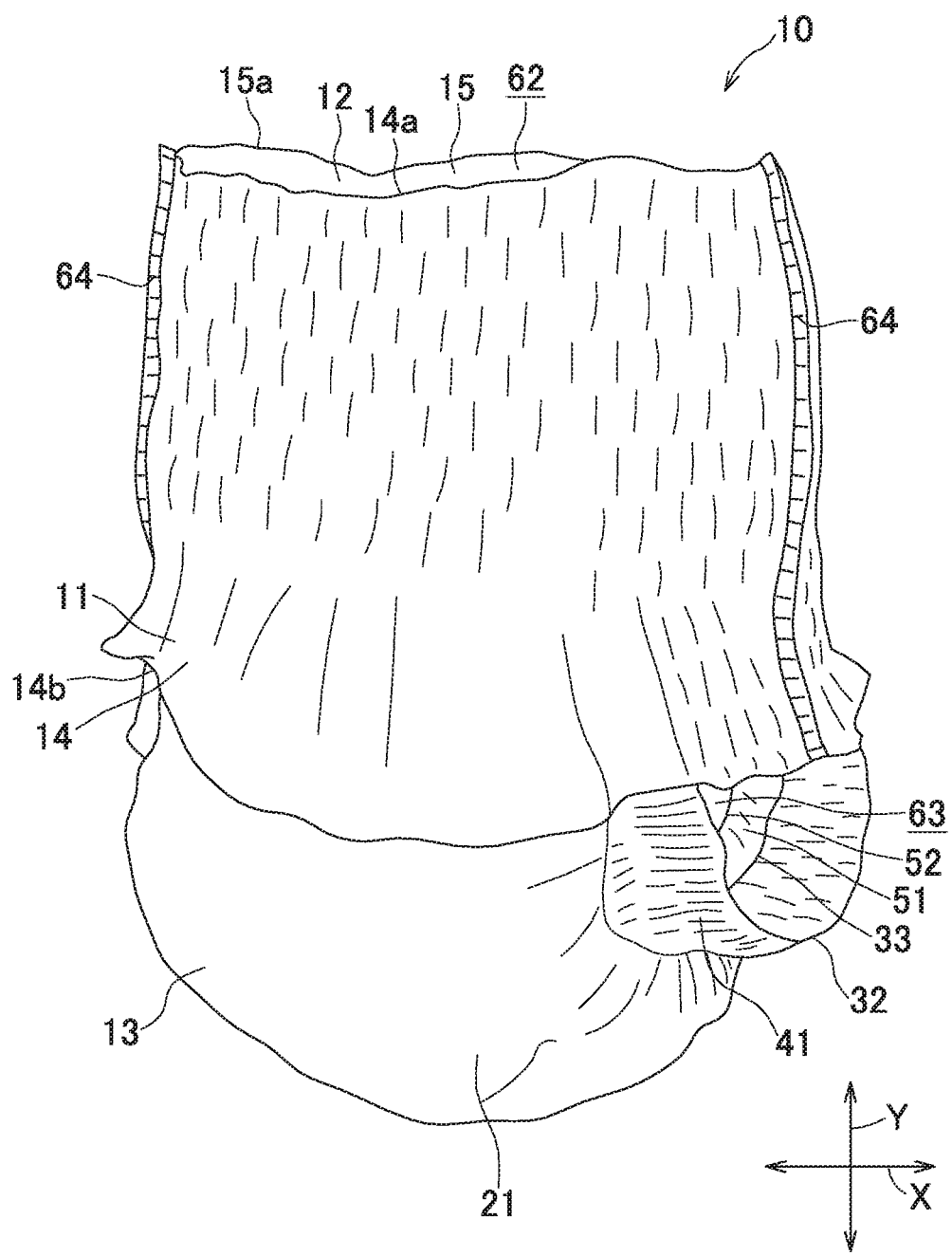
FIG. 1 Perspective view of a disposable diaper according to the present invention.
Figure 2:
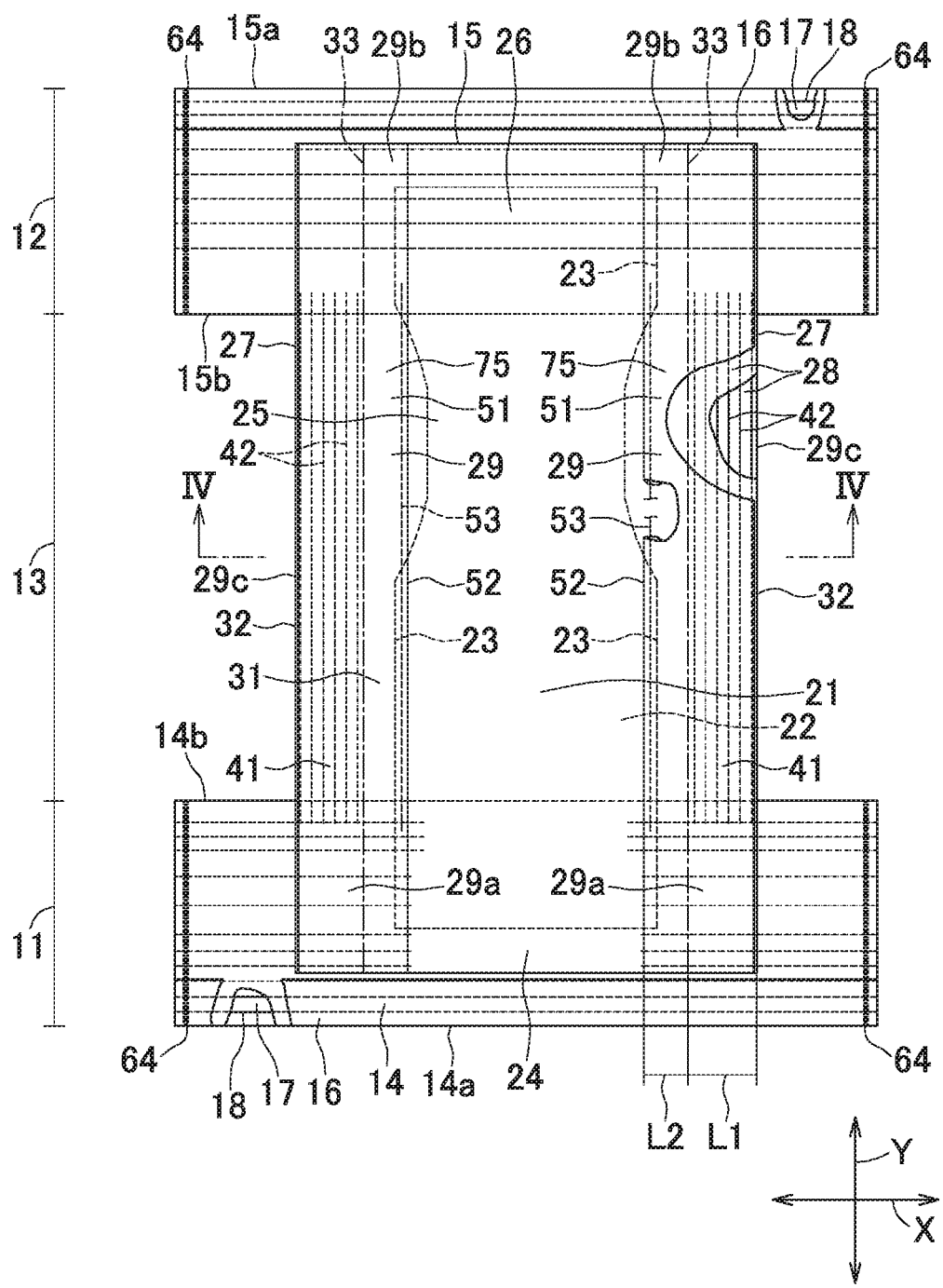
FIG. 2 Partially cutaway opened view of the disposable diaper of FIG. 1.
Figure 3:
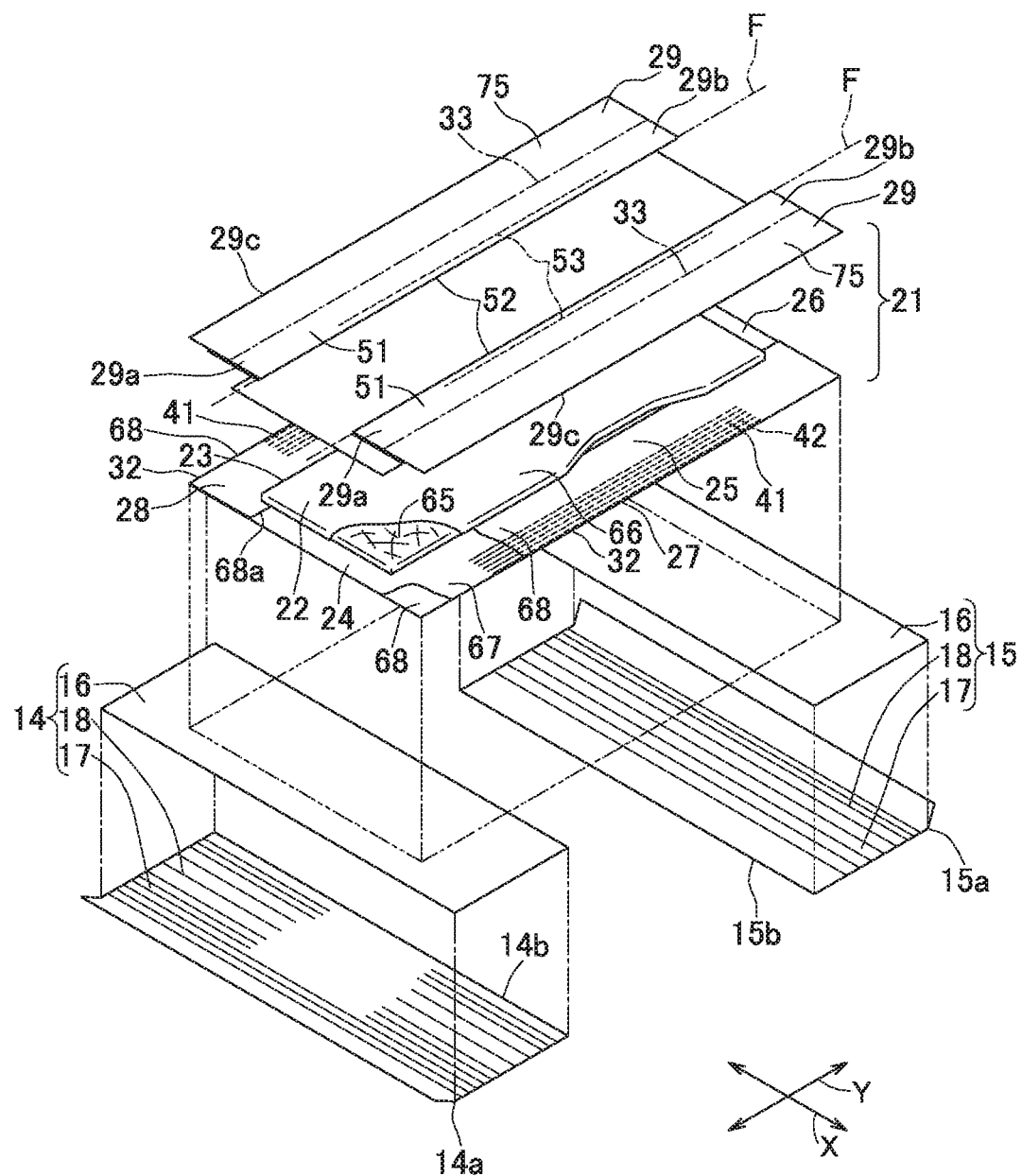
FIG. 3 Partially cutaway exploded perspective view of the disposable diaper of FIG. 1.

Referring to FIG. 1 through FIG. 3, a diaper 10 may include a front waist region 11, a rear waist region 12, a crotch region 13 extending between the front and rear waist regions 11, 12 and a vertically long absorbent chassis 21 extending toward the front and rear waist regions 11, 12 centering on the crotch region 13. As illustrated in FIGS. 2 and 3, the absorbent chassis 21 may include an absorbent structure 22 and a pair of side flaps 31 extending outward in a lateral direction X from both side edges 23, 23 of the absorbent structure 22. Meanwhile, a direction orthogonal to the lateral direction X of the diaper 10 is denoted as a vertical direction Y in the present specification.

According to the present embodiment, the front waist region 11 and the rear waist region 12 may respectively be formed of a front waist panel 14 and a rear waist panel 15. The rear waist panel 15 and the front waist panel 14 are rectangular sheet materials each defined by an interior sheet 16, an exterior sheet 17 and a plurality of waist elastic threads 18 joined therebetween under tension in the lateral direction X. A front end 24 and a rear end 26 of the rectangular absorbent chassis 21 respectively defined by both ends in the vertical direction Y of the rectangular absorbent chassis 21 are fixed to respective midparts in the lateral direction X of the front waist panel 14 and the rear waist panel 15. The crotch region 13 is defined by an intermediate region 25 extending between the front end 24 and the rear end 26 of the absorbent chassis 21.

The front waist panel 14 and the rear waist panel 15 are joined to each other by adhesive bonding or heat sealing along seam areas 64 located on both sides in the lateral direction X and extending in the vertical direction Y of the respective panels 14, 15. In this way, a waist-opening 62 and a pair of leg-openings 2 are defined, and whereby the diaper 10 of pant-type (also known as pull-on type) as illustrated in FIG. 1 is constructed. More specifically, the waist-opening 62 is defined by respective upper edges 14a, 15a of the front and rear waist panels 14, 15 and the leg-openings 63 are defined by parts of lower edges 14b, 15b of the front and rear waist panels 14, 15 located lateral to the absorbent chassis 21 in the lateral direction X together with side edges 27 of the intermediate region 25 of the absorbent chassis 21.

Materials for the interior sheet 16 and the external sheet 17 may include, nonwoven fabrics or resinous films well known in the relevant technical field of the present invention. Materials for the waist elastic threads 18 may include, well known elastic threads, for example, polyurethane series elastic threads. When the waist elastic threads 18 are adhesively secured to the interior and exterior sheets 16, 17, hot melt adhesives well known in the relevant technical field may be used. As the absorbent structure 22 located in the absorbent chassis 21, well-known absorbent structures for the diaper, for example, the absorbent structure 22 including an absorbent core 65 containing superabsorbent polymer particles and/or fluff pulp (not shown) and wrapped with a liquid-permeable sheet 69 such as tissue paper may be used.

The absorbent chassis 21 according to the present embodiment has a body-facing surface and a non-body-facing surface opposed to the former and may include the absorbent structure 22, a body-side liner 66 located on the body-facing surface of the absorbent structure 22, an exterior composite sheet 28 located on the non-body-facing surface of the absorbent structure 22 so as to extend in the lateral direction X beyond both side edges of the absorbent structure 22 and a pair of body-side composite sheets 29 respectively located on the outer sides in the lateral direction X of the absorbent structure 22 and joined to the body-facing surface of the exterior composite sheet 28. In this regard, the paired side flaps 31 extending outward from both side edges 23, 23 in the lateral direction X of the absorbent structure 22 may respectively be formed of laminated sheet materials including the parts of the exterior composite sheet 28 extending outward in the lateral direction X beyond both side edges of the absorbent structure 22 and the paired body-side composite sheets 29.

Each of the side flaps 31 may include a distal edge 32 spaced apart in the lateral direction X from the side edge 23 of the absorbent structure 22 and extending in the vertical direction Y, a cuff branch line 33 located between the side edge 23 of the absorbent structure 22 and the distal edge 32 and extending in the vertical direction Y, a leg-opening elasticized area 41 extending between the cuff branch line 33 and the distal edge 32, and a leakage-barrier cuff 51 branched from the cuff branch line 33 and extending in a direction intersecting with the leg-opening elasticized area 41. The leakage-barrier cuff 51 has a free edge 52 parallelly-spaced apart inward in the lateral direction X from the cuff branch line 33 so as to extend in the vertical direction Y. The cuff branch line 33 is denoted by a dashed-dotted line in FIGS. 2 and 3.

The exterior composite sheet 28 may include a rectangular leakage-barrier sheet formed of a plastic film 67 located on the non-body-facing surface of the absorbent structure 22 so as to extend outward in the lateral direction X beyond the absorbent structure 22 and a rectangular backsheet 68 located on the non-body-facing surface of the leakage-barrier sheet 67 so as to extend outward in the lateral direction X beyond the absorbent structure 22. A dimension in the lateral direction of the leakage-barrier sheet 67 is the same as or slightly smaller than a dimension in the lateral direction X of the absorbent chassis 21. A dimension in the lateral direction X of the backsheet 68 is larger than the dimension in the lateral direction X of the leakage-barrier sheet 67. Parts of the backsheet 68 extending outward in the lateral direction X beyond both side edges of the leakage-barrier sheet 67 are folded back inward along side edges 67a of the leakage-barrier sheet 67 and joined to the body-facing surface of the leakage-barrier sheet 67. The fold lines along which the backsheet 68 are folded back along the side edges 67a of the leakage-barrier sheet 67 correspond to the distal edge 32 of the side flaps 31.

Of the backsheet 68 folded back, both distal ends 68a in the vertical direction Y are located beneath the non-body-contact surface of the absorbent structure 22 and fixed between the absorbent structure 22 and the leakage-barrier sheet 67. Between the leakage-barrier sheet 67 and the backsheet 68 folded back, a plurality of leg-elastic members 42 are contractibly secured under tension in the vertical direction Y. The stretch ratio of the leg-elastic members 42 may be uniform or gradually lower in the lateral direction X from the cuff branch lines 33 toward the distal edges 32. The leg-elastic members 42 are located in the intermediate region 25 of the absorbent chassis 21 so as to extend toward the front end 24 and the rear end 26. Both ends of the leg-elastic members 42 are secures to the front end 24 and the rear end 26 of the absorbent chassis 21 with hot melt adhesives. The backsheet 68 and the leakage-barrier sheet 67 may be formed of well-known sheet materials. For example, the leakage-barrier sheet 67 may be formed of plastic films and the backsheet 68 may be formed of fibrous nonwoven fabrics.

Each of the paired body-side composite sheets 29 may include a vertically long nonwoven fabric strip 75 and at least one cuff-elastic member 53. A dimension in the vertical direction Y of the nonwoven fabric strip 75 may be the same as or smaller than a dimension in the vertical direction Y of the absorbent chassis 21. Adjacently to fold back lines F, the cuff-elastic members 53 are contractibly secured under tension in the vertical direction Y to the interior side of the nonwoven fabric strip 75 folded back along the fold-back lines F. More specifically, in the body-side composite sheet 29 according to the present embodiment, the cuff-elastic members 53 are joined between bilaminar sheet materials. In addition, the fold back lines F correspond to the free edges 52 of the respective leakage-barrier cuffs 51.

The body-side composite sheets 29 are respectively joined to the body-facing surfaces of the backsheet 68 extending in the lateral direction X beyond both side edges 23 of the absorbent structure 22. More specifically, the body-side composite sheets 29 have the outer edges 29c extending in the vertical direction Y in parallel to the fold back lines F and respective regions defined between the outer edges 29c of the respective body-side composite sheets 29 and the fold back lines F, rather in adjacent to the fold back lines F are joined to the body-facing surface of the backsheets 68. Likewise, both ends 29a, 29b in the vertical direction Y of the body-side composite sheets 29 are also joined to the body-facing surface of the respective backsheets 68. In this way, the parts of the body-side composite sheet 69 not joined to the backsheets 68 function as the leakage-barrier cuffs 51. The body-side composite sheets 29 and the backsheets 68 is joined preferably with hot melt adhesives (not shown). However, it is also possible to join the body-side composite sheets 29 to the backsheets 68 by heat sealing. Meanwhile, the body-side composite sheets 29 are not joined to the body-side liner 66 of the absorbent structure 22.

The outer edges 29c of the body-side composite sheets 29 joined to the backsheets 68 nearly coincide with the fold lines of the backsheets 68, i.e., the distal edges 32 of the respective side flaps 31, or keep a distance from the distal edges 32 of the side flaps 31. In the body-side composite sheets 29 joined to the backsheets 68, border lines between the parts joined to the backsheets 68 and the parts not joined to the backsheets 68 define the cuff branch lines 33 extending in the vertical direction Y and areas extending from the cuff branch lines 33 to the fold back lines F, i.e., to the free edges 52 of the leakage-barrier cuffs 51 define the leakage-barrier cuffs 51. Meanwhile, in the body-side composite sheets 29, areas extending from the cuff branch lines 33 to the distal edges 32 of the respective side flaps 31 are included by the leg-opening elasticized areas 41. According to the present invention, the distance L1 from the respective cuff branch lines 33 to the respective distal edges 32 is longer than the distance L2 from the respective cuff branch lines 33 to the respective free edges 52. According to the present embodiment, as will be apparent from the above description, the leakage-barrier cuffs 51 may be formed separately from the leg-opening elasticized areas 41 so that, along the cuff branch lines 33, the leakage-barrier cuffs 51 and the leg-opening elasticized areas 41 may be joined together by heat sealing or adhesive bonding.

Referring to FIG. 1, during use of the diaper 10, the cuff-elastic members 53 secured to the leakage-barrier cuffs 51 adjacently to the free edges 52 thereof constrict so as to raise the leakage-barrier cuffs 51 around the respective cuff-branch lines 33 as base ends away from the absorbent structure 22 until the leakage-barrier cuffs 51 fit to the wearer's inguinal area, thereby preventing the body exudates from leaking out from the diaper 10. In the present embodiment, as illustrated in FIG. 2, the distance L1 from the cuff branch line 33 to the distal edge 32 is larger than the distance L2 from the cuff branch line 33 to the free edge 52. This makes it possible to prevent the movements of the wearer's legs from dragging the leakage-barrier parts 51 out from the diaper 10 beyond the leg-opening elasticized areas 41. The distance L2 from the cuff branch line 33 to the free edge 52 is preferably in a range of 50% to 90% of the distance L1 from the cuff branch line 33 to the distal edge 32. In addition, according to the present embodiment, the front end 24 and the rear end 26 respectively defined by both ends in the vertical direction Y of the absorbent chassis 21 are respectively fixed to the front waist region 11 and the rear waist region 12 and the parts of the respective leg-opening elasticized areas 41 located in the front end 24 and the rear end 26 are fixed to the front waist region 11 and the rear waist region 12 so as to be outward-directed in the lateral direction X of the absorbent chassis 21. Meanwhile, the parts of the leakage-barrier cuffs 51 located in the front end 24 and the rear end 26 are fixed to the front waist region 11 and the rear waist region 12 so as to be inward-directed in the lateral direction X of the absorbent chassis 21. By fixing the leg-opening elasticized areas 41 so as to be outward-directed in the lateral direction X and fixing the leakage-barrier cuffs 51 so as to be inward-direction in the lateral direction X. The leakage-barrier cuffs 51 may reliably be prevented from being dragged out from the diaper 10 beyond the leg-opening elasticized areas 41. If the leakage-barrier cuffs 51 are dragged out from the diaper 10, a leakage-barrier of the leg-opening elasticized areas 41 does not sufficiently function. From this viewpoint, the leakage-barrier cuffs 51 are preferable to be prevented from being dragged out from the diaper 10. In addition, by preventing the leakage-barrier cuffs 51 from being dragged out from the diaper 10, it is ensured that the leakage-barrier cuffs 51 cooperate with the leg-opening elasticized areas 41 to exhibit a double leak-barrier function. Thus, the function of the leakage-barrier cuffs 51 should not be hindered.

Figure 4:
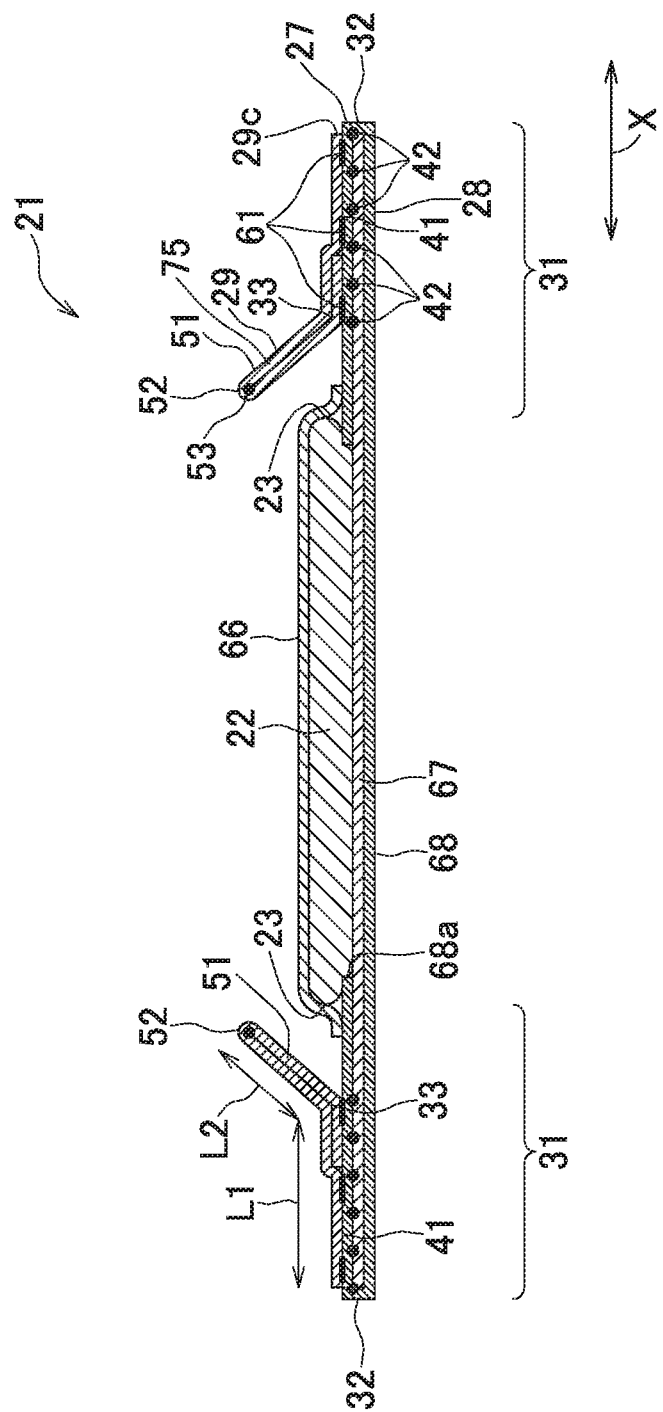
FIG. 4 Sectional view taken along line IV-IV in FIG. 1.

As illustrated in FIG. 1, the leg-opening elasticized areas 41 cylindrically project outward from the diaper 10 whereby the leg-opening elasticized areas 41 extensively and closely fit around the wearer's thighs. In addition, as illustrated in FIG. 4, in the present embodiment, each of the leg-opening elasticized areas 41 may include four sheet material layers and each of the leakage-barrier cuffs 51 may include two sheet material layers. The fact that the number of the sheet material layers defining the respective leg-opening elasticized areas 41 is larger than the number of the sheet material layers defining the respective leakage-barrier cuffs 51 results in that a stiffness of the respective leg-opening elasticized areas 41 is relatively high and inhibits a possibility that the leg-opening elasticized areas 41 cylindrically projecting outward from the diaper 10 may be constricted as folded into a bellowslike shape in the lateral direction X. Thus, even when the wearer moves his or her legs, clearance gaps should not be left between the leg-opening elasticized areas and the wearer's thighs. In this way, leakage of body exudates may be prevented. The inhibiting effect against the possibility that the leg-opening elasticized areas 41 cylindrically projecting outward from the diaper 10 may be constricted in the lateral direction X as folded into a bellowslike shape makes it also possible to inhibit a possibility that gather marks may be left on the wearer's thighs. Meanwhile, according to the present invention, as used herein, the term "the leg-opening elasticized areas 41 have relatively high stiffness" means that these elasticized areas 41 are not easily deformed in the lateral direction X of the diaper 10.

The parts of the body-side composite sheets 29 defining the leakage-barrier cuffs 51 are defined by two layers of nonwoven fabrics. However, it is not imperative for each of the body-side composite sheets 29 to be defined by two layers of nonwoven fabrics also along the outer edges 29c also but, as illustrated by FIG. 4, each of the body-side composite sheets 29 may be defined by a single nonwoven fabric along the outer edges 29c. In other words, one of two layers of nonwoven fabrics defining the body-side composite sheets 29 may extend into the leg-opening elasticized areas 41 so as to be included therein. In consequence, the number of the sheet material layers defining the respective leg-opening elasticized areas 41 increases and whereby the stiffness of the respective leg-opening elasticized areas 41 is enhanced. In addition, the nonwoven fabrics extending from the respective body-side composite sheet 29 to the leg-opening elasticized areas 41 is preferably joined to the sheet material located on the body-facing surface of the leg-opening elasticized areas 41 by adhesive bonding or heat sealing whereby the stiffness of the leg-opening elasticized areas 41 is further enhanced. To enhance the stiffness of the leg-opening elasticized area 41 sufficiently, a width dimension of an area in which the sheet material extending from the respective body-side composite sheets 29 to the respective leg-opening elasticized areas 41 overlap the respective leg-opening elasticized areas 41 is preferably at least 80% of a distance from the respective cuff branch lines 33 to the respective distance edges 32. In addition, at least one sheet material layer may be extended toward the leg-opening elasticized areas 41 until both ends of the sheet material nearly coincides with the distal ends of the respective leg-opening elasticized areas 41, namely, the distal edges 32 of the respective side flaps 32.

In order to enhance the stiffness of the leg-opening elasticized areas 41, the sheet materials defining each of the elasticized areas 41 are preferably joined together by adhesive bonding or heat sealing. The hot melt adhesives or the heat sealing used to join the sheet materials contribute to enhance the stiffness of the leg-opening elasticized areas 41 thereby restricting further effectively, the possibility that the leg-opening elasticized areas 41 may be constricted in the lateral direction X as folded into a bellowslike shape. FIG. 4 exemplarily illustrates an instance in which the sheet materials included in the leg-opening elasticized areas 41 are joined together with hot melt adhesive 61. When the hot melt adhesive 61 is used to join the sheet materials included in each of the elasticized areas 41 to each other, the hot melt adhesive 61 is preferably distributed linearly in a direction intersecting with the leg-elastic members 42 (the direction including the lateral direction components). By distributing the hot melt adhesive 61 in the direction intersecting with the leg-elastic members 42 extending in the vertical direction Y, during use of the diaper 10, the leg-opening elasticized areas 41 may be constricted in the lateral direction X as folded into a bellowslike shape. As specific examples of a distributing pattern for the hot melt adhesives, a spiral-pattern or a wave-pattern is also useful. Meanwhile, to facilitate understanding, only a portion of the hot melt adhesives used to join the sheet materials is illustrated in FIG. 4. Referring to FIG. 4, the hot melt adhesives may be distributed between the sheet materials at optional locations.

As described previously, both ends of the plurality of leg-elastic members 42 located in the leg-opening elasticized areas 41 so as to extend in the vertical direction Y are respectively secured to the front end 24 and the rear end 26 of the absorbent chassis 21. In this manner, the leg-elastic members 42 also function to inhibit the possibility that the leg-opening elasticized areas 41 may be constricted in the lateral direction X as folded into a bellowslike shape. Specifically, the number of the leg-elastic members 42 may be increased and whereby the interval thereof may be closed to inhibit the possibility that the leg-opening elasticized areas 41 may be constricted as folded into a belllowslike shape. More specifically, the number of the leg-elastic members 42 for each of the leg-openings is preferably four or more and, more preferably, six or more. In addition, a plurality of the leg-elastic members 42 are arranged preferably at intervals of 6 mm or less, more preferably at intervals of 5 mm or less. As material for the leg-elastic members 42, for example, elastic threads of polyurethane series having fineness in a range of about 300 through about 940 dtex may be used but not limited thereto. For example, elastic nonwoven fabrics or elastic sheets may be used in the place of the elastic threads of polyurethane series. A stretch ratio of these elastic members is typically in a range of 2.0 to 2.3 but not limited to such values.

Preferably, the cuff branch lines 33 are located lateral to the absorbent structure 22 in the lateral direction X and the sheet materials included in the leakage-barrier cuffs 51 are extended into the respective leg-opening elasticized areas 41. Whereby, the number of sheet material layers included by a region defined between the side edges 23 of the absorbent structure 22 and the respective cuff branch lines 33 becomes less than the number of sheet material layers included by areas extending from the respective cuff branch lines 33 to the distal edges 32, i.e., the number of sheet material layers included by the respective leg-opening elasticized areas 41. The number of sheet material layers being different on both sides of the respective cuff branch lines 33 in this manner facilitates the leg-opening elasticized areas 41 to be bent along the respective cuff branch lines 33, thereby facilitating these elasticized areas 41 to project outward from the diaper 10. In addition, the leg-opening elasticized areas 41 raise the absorbent structure 22 by the cuff branch lines 33 extending in the vertical direction Y in the vicinity of the absorbent structure 22, thereby making it easy to move the absorbent structure 22 closer to the wearer's body. A distance from the side edges 23 of the absorbent structure 22 to the respective cuff branch lines 33 is preferably in a range of 5% to 30% of a distance from the respective cuff branch lines 33 to the respective distal edges 32. Meanwhile, dimensions of the respective parts of the diaper 10 are measured in a state of the diaper 10 planarly developed, as exemplarily illustrated in FIG. 2, until no crease is left on the surface of the diaper 10.

Preferably, in each of the side flaps 31, a single leg-elastic member 42 is located so as to be overlapped with the cuff branch line 33. As described previously, the stretch ratio of a plurality of the leg-elastic members 42 is set to be uniform or gradually decreases in the lateral direction X from the cuff branch line 33 toward the distal edge 32. Thus, a contraction degree of the leg-elastic members 42 during use of the diaper 10 gradually decreases from the cuff branch line 33 to the distal edge 32 or uniform. Consequently, during use of the diaper 10, the area extending from the cuff branch line 33 to the distal edge 32, i.e., the leg-opening elasticized area 41 projects outward from the diaper 10 in the form of a frustum of a circular cone having a diameter gradually enlarging or a circular cylinder. In addition, the single leg-elastic member 42 located so as to be overlapped with the cuff branch line 33 ensures that the base end of the leakage-barrier cuff 51 is put in close contact with the wearer's thigh, thereby preventing the body exudates from leaking out.

Figure 5A:
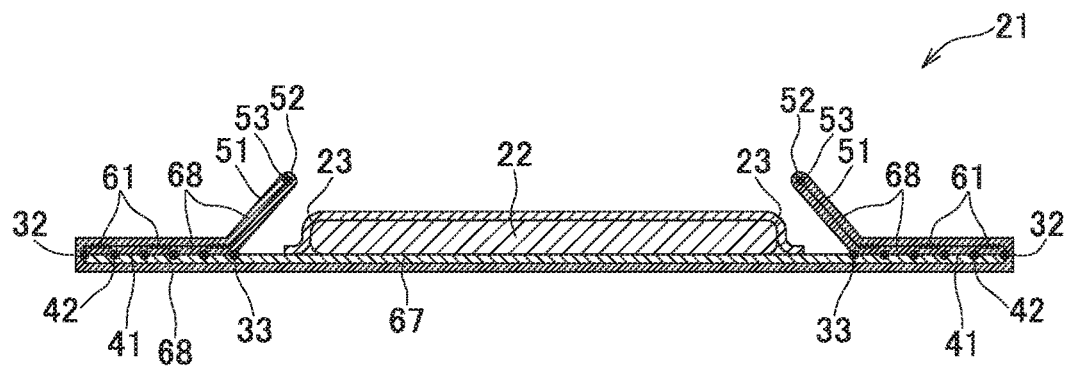
FIGS. 5A to 5C Sectional views illustrating alternatives of the present invention.

While the present invention has been described with reference to FIGS. 1 through 4, the present invention is not limited thereto and may include the various alternatives. For example, as illustrated in FIG. 5A, the leakage-barrier cuff 51 and the leg-opening elasticized area 41 may be formed as a unit instead of forming from the layered sheet materials separately prepared. In the alternative illustrated in FIG. 5A, the backsheet 68 made of a single nonwoven fabric is folded back, and whereby the leakage-barrier cuff 51 and the leg-opening elasticized area 41 are unified. Instead of the alternative illustrated in FIG. 5A, it is also possible to locate a sheet material laminate unified from the leakage-barrier cuff 51 and the leg-opening elasticized area one by one on both sides in the lateral direction X of the absorbent structure 22. In other words, it is possible to forma pair of the side flaps 31 each constituted of the leakage-barrier cuff 51 and the leg-opening elasticized area 41 prepared separately from the absorbent structure 22. Furthermore, it is also possible to fold back the backsheet 68 formed of a single layer of nonwoven fabrics to form the leakage-barrier cuff 51 and the leg-opening elasticized area 41 wherein the number of times for folding back the sheet material is increased in comparison with the instance illustrated in FIG. 5A so that the number of sheet material layers included by the leg-opening elasticized area 41 may be larger than the number of sheet material layers included by the leakage-barrier cuff 51.

Figure 5B:
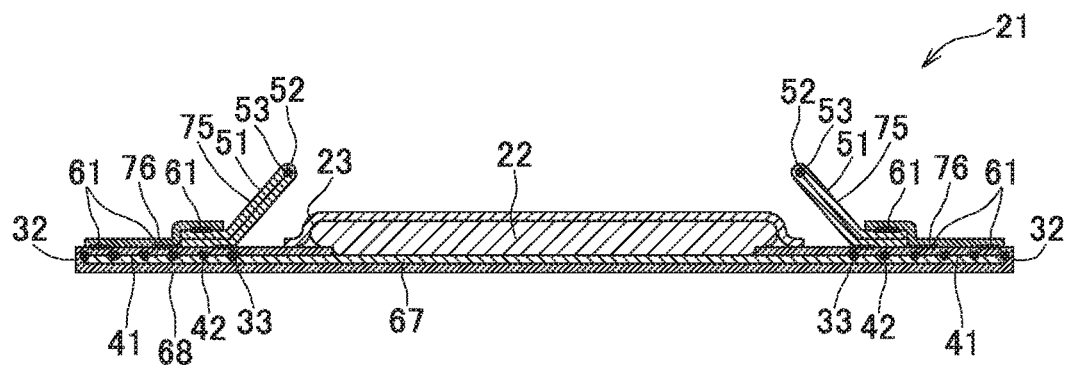
Figure 5C:
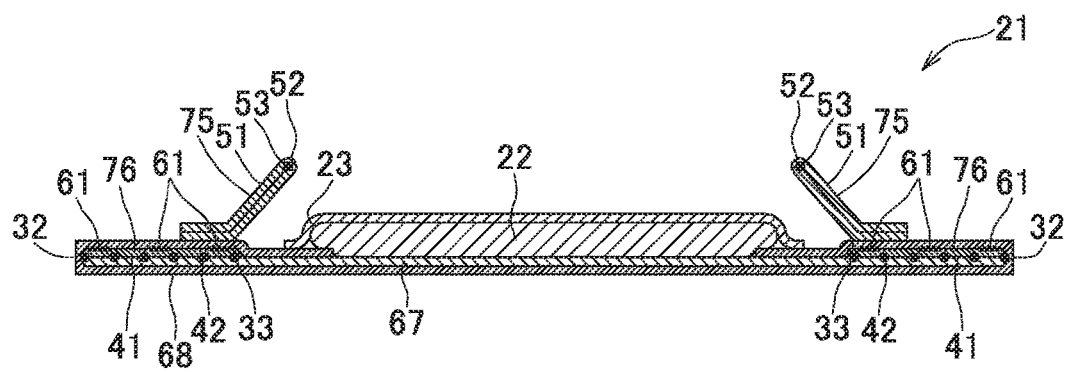

As further another alternative, a reinforcing sheet 76 prepared separately from the leg-opening elasticized area 41 may be joined to the elasticized area 41 with the hot melt adhesives 61 as illustrated in FIG. 5B and FIG. 5C. The reinforcing sheet 76 may be formed of nonwoven fabrics or plastic sheets. The reinforcing sheet 76 may be located on arbitrary region of the sheet material laminate constructing the leg-opening elasticized areas 41. FIG. 5B illustrates an example wherein the reinforcing sheet 76 is located on the body-facing surface of the leg-opening elasticized area 41. FIG. 5C illustrates an example wherein the reinforcing sheet 76 is interlaid in the sheet material laminate forming the leg-opening elasticized area 41. Furthermore, it is also possible to locate the reinforcing sheet 76 on the non-body-facing surface of the leg-opening elasticized area 41 (not illustrated). Meanwhile, only a portion of hot melt adhesive 61 used to join the sheet materials to each other is illustrated in FIG. 5A through FIG. 5C in order to facilitate understanding. In FIG. 5A through FIG. 5C, the hot melt adhesives may be distributed between an arbitrary pair of sheet members.

In the illustrated embodiment, the leakage-barrier sheet 67 is spaced apart in the lateral direction X from the distal edge 32 of the side flaps 31. This makes it possible to inhibit a possibility that the distal edge 32 of the side flaps 31, i.e., the distal edge 32 of the leg-opening elasticized area may become excessively stiff and irritate the wearer's skin. However, the leakage-barrier sheet 67 may extend to the distal edge 32 of the side flaps 31. In addition, while the front and rear waist panels 14, 15 are formed of the nonwoven fabrics and the waist-elastic threads 18, the front and rear waist panels 14, 15 may be formed of a rectangular elastic nonwoven fabric and the elastic threads may be omitted.

The invention claimed is:

1. A disposable diaper, comprising:
a front waist region, a rear waist region and a crotch region located between the front and rear waist regions and includes a vertically elongated absorbent chassis extending toward the front and rear waist regions and centering on the crotch region,
wherein
the absorbent chassis includes an absorbent structure and a pair of side flaps extending outward in the lateral direction from both side edges of the absorbent structure,
each of the side flaps is formed of layered sheet materials and includes
a distal edge being spaced apart in the lateral direction from the side edge of the absorbent structure and extending in the vertical direction,
a cuff branch line defined between the side edge of the absorbent structure and the respective distal edge so as to extend in the vertical direction,
a leg-opening elasticized area extending between the cuff branch line and the distal edge and a leakage-barrier cuff branched from the cuff branch line and extending in a direction intersecting with the leg-opening elasticized area,
the leg-opening elasticized area has a plurality of leg-elastic members extending in the vertical direction and at a predetermined interval in the lateral direction,
the leakage-barrier cuff has a free edge parallelly-spaced in the lateral direction from the cuff branch line so as to extend in the vertical direction,
a distance from the cuff branch line to the distal edge is larger than a distance from the cuff branch line to the free edge,
the number of sheet material layers included in the leg-opening elasticized area is larger than the number of the sheet material layers included in the leakage-barrier cuff, and
a single leg-elastic member, among the plurality of leg-elastic members, overlaps the cuff branch line in a thickness direction perpendicular to the lateral direction and the vertical direction.

* * * * *